(12) United States Patent
Jones et al.

(10) Patent No.: US 7,347,200 B2
(45) Date of Patent: Mar. 25, 2008

(54) MEDICAMENT DISPENSER

(75) Inventors: Anthony Patrick Jones, Ware (GB); Andrew Paul Horton, Ware (GB); Richard William Hartley, Ware (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 72 days.

(21) Appl. No.: 10/415,279

(22) PCT Filed: Oct. 19, 2001

(86) PCT No.: PCT/EP01/12108

§ 371 (c)(1), (2), (4) Date: Mar. 1, 2004

(87) PCT Pub. No.: WO02/36190

PCT Pub. Date: May 10, 2002

(65) Prior Publication Data

US 2005/0076904 A1    Apr. 14, 2005

(30) Foreign Application Priority Data

Oct. 31, 2000    (GB) .................................. 0026646.0

(51) Int. Cl.
*A61M 11/00* (2006.01)
(52) U.S. Cl. ............................. 128/200.23; 128/205.23
(58) Field of Classification Search ........... 128/200.14, 128/200.23, 202.27, 203.12, 205.23
See application file for complete search history.

(56) References Cited

U.S. PATENT DOCUMENTS

| 4,518,861 | A | | 5/1985 | Krempl |
| 4,900,303 | A | | 2/1990 | Lemelson |
| 5,452,711 | A | | 9/1995 | Gault |
| 5,468,961 | A | | 11/1995 | Gradon et al. |
| 5,502,434 | A | | 3/1996 | Minowa et al. |
| 5,544,647 | A | | 8/1996 | Jewett et al. |
| 5,622,163 | A | | 4/1997 | Jewett et al. |
| 5,794,612 | A | * | 8/1998 | Wachter et al. ......... 128/200.23 |
| 5,809,997 | A | * | 9/1998 | Wolf ..................... 128/200.23 |
| 6,011,478 | A | | 1/2000 | Suzuki et al. |
| 6,029,659 | A | | 2/2000 | O'Connor |

FOREIGN PATENT DOCUMENTS

| DE | 3 901 963 | 8/1990 |
| DE | 199 34 582 | 1/2001 |
| EP | 0689848 | 1/1996 |
| FR | 2 257 351 | 8/1975 |
| GB | 2 340 407 | 2/2000 |
| GB | 2 342 874 | 4/2000 |
| JP | 02009856 | 1/1990 |
| WO | WO95/07723 | 3/1995 |
| WO | WO95/07724 | 3/1995 |
| WO | WO99/65551 | 12/1999 |
| WO | WO 00/01612 | 1/2000 |
| WO | WO 00/16836 | 3/2000 |
| WO | 0055072 | 9/2000 |
| WO | WO 01/85241 | 11/2001 |
| WO | WO 02/36190 | 5/2002 |

* cited by examiner

*Primary Examiner*—Steven O. Douglas
(74) *Attorney, Agent, or Firm*—James P. Riek

(57) ABSTRACT

A medicament dispenser comprising: (i) a housing having an outlet; (ii) a medicament container locatable within said housing; (iii) an electronic dose counter associated with said outlet, wherein said dose counter comprises a first sensor for directly detecting a medicament release dispensible from said medicament container through said outlet is disclosed.

32 Claims, 11 Drawing Sheets

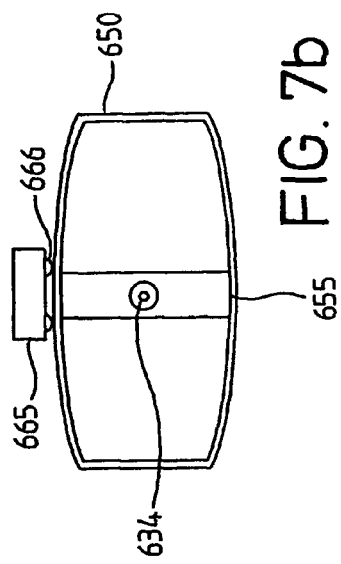
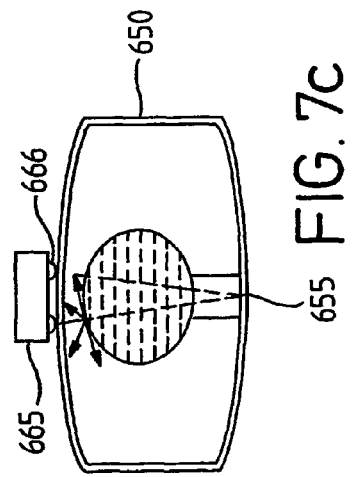
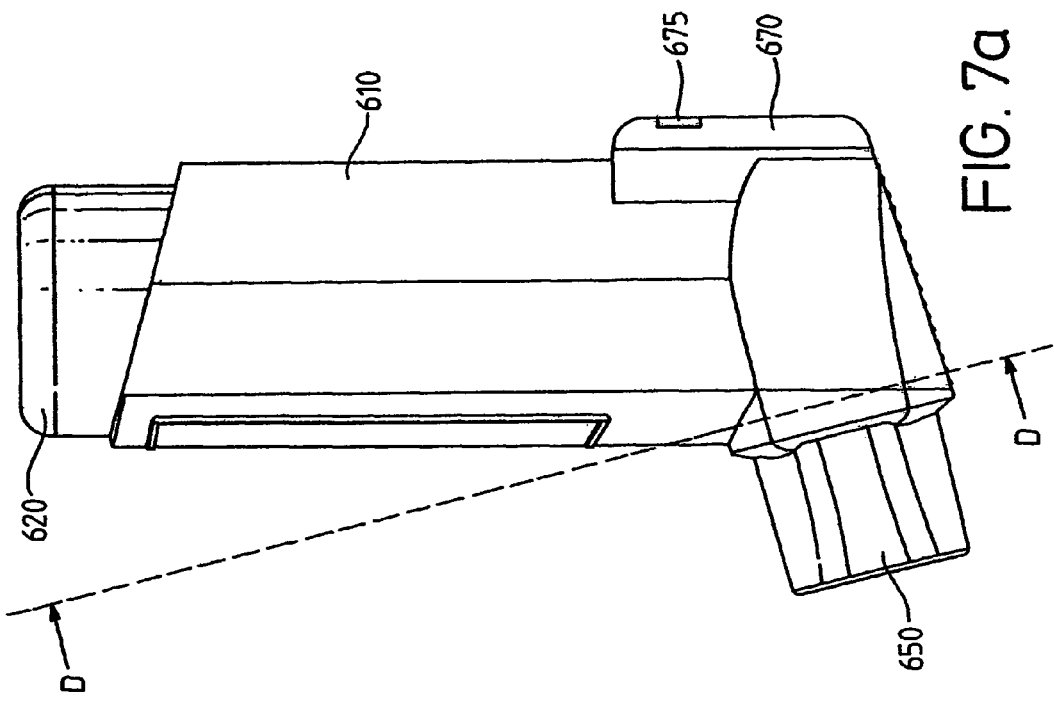

MEDICAMENT DISPENSER

This application is filed pursuant to 35 USC 371 as a United States National Phase Application of International Patent Application Ser. No. PCT/EP01/12108 filed 19 Oct. 2001, which claims priority from GB 0026646.0 filed on 31 Oct. 2000 in the United Kingdom.

This invention relates to medicament dispenser, particularly dry powder and metered dose inhalation devices, which have dose counters attached thereto. In particular, the invention relates to sensors used with dose counters to detect and validate release of medicament from the dispenser.

BACKGROUND OF THE INVENTION

Medicaments for treating respiratory disorders are frequently administered as dry powder formulations through the mouth and nose. Dry powder inhalation devices, or inhalers, are used in the administration of these drugs, inhalation by the patient resulting in uptake of a specified dosage of medicament through the nose or mouth.

The drug may be stored as a dry powder within a reservoir in the body of the inhaler, a metering chamber being utilised to administer a specified dose of medicament. Alternatively, more sophisticated inhalation devices employ medicament carriers, such as individual capsules or blister packs/strips containing defined doses of powdered drug.

It is also known to use for such therapy medicaments which are contained in an aerosol and are administered to a patient by means of an inhalation device. The aerosol containers used in such inhalation devices are designed to deliver a predetermined dose of medicament upon each actuation and are known as Metered Dose Inhalers (MDIs); see Peter Byron, Respiratory Drug Delivery, CRC Press, Boca Raton, Fla. (1990) for a general background on this form of therapy.

Mechanical and electrical dose indicating devices, which typically count the number of doses delivered from or remaining in the medicament dispenser, are frequently used in dry powder inhalers and MDIs to enable patients to determine how much medicament is available in the dispenser for future use.

One problem associated with both mechanical and electrical dose counters is that they may, on occasions, give false readings. Thus the electronic dose counter disclosed in U.S. Pat. No. 5,020,527 employs a mechanical trigger, which may be actuated without release of the medicament, thereby giving a false reading. Other forms of triggers are also known, particularly the use of sensing means to detect actuation of the dispenser.

U.S. Pat. No. 5,544,647 discloses a range of sensors which may be used to detect and record actuation of MDIs. Typical sensors include pressure switches which are sensitive to either physical contact with a movable element of the device or to the inward breath of the patient. Other examples include sensors which are responsive to light, such as reflected or emitted light, or optical sensors which recognise reference points on the container or housing. These sensors are designed to detect movement of the aerosol container following actuation of the device by being aligned to a reference point or a light source, such as a LED. Sensors which are responsive to electromagnetic radiation, such as fluctuations in electromagnetic fields caused by movement of the container, are also disclosed within this document.

WO 95/07724 describes a dry powder inhaler with an electronic dose counter which employs a series of sensors to validate actuation of the inhaler. The inhaler uses magnetically responsive proximity reed switches to detect medicament loading within the device, and a thermistor sensor to detect temperature changes due to inhalation by the patient.

A general problem encountered with dose counters in the art, such as those described above, is that they are dependent upon sensors which do not directly detect the medicament release from the dispenser. All of the sensors used in the art are arranged to sense some feature associated with actuation of the device, such as movement of the container/housing or pressure/temperature changes due to inhalation. This indirect method of sensing medicament release can lead to false readings being registered on the dose counter, if for example the sensor is activated without release of medicament. Accidental activation or triggering of the sensor may, for example, result from partial movement of the container or from interference with light received by the sensor. Similarly, a blockage or only partial release of the drug from either an MDI or dry powder inhaler would lead to a false reading registering on the dose counter.

SUMMARY OF INVENTION

It is an object of the present invention to provide direct sensing means by which release of a medicament can be detected and recorded on a dose counter.

It is a further object of the present invention to provide a means of confirming or validating medicament release from a medicament dispenser.

DETAILED DESCRIPTION OF INVENTION

According to the present invention there is provided a medicament dispenser comprising:
 (i) a housing having an outlet;
 (ii) a medicament container locatable within said housing;
 (iii) an electronic dose counter associated with said outlet;
  wherein said dose counter comprises a first sensor for directly detecting a medicament release dispensible from said medicament container through said outlet.

In one aspect, the first sensor comprises an emitter and a detector. In a second aspect, the sensor comprises only a detector, for example a pyroelectric detector which responds to a decrease in temperature.

Suitably, the emitter emits electro magnetic radiation and the detector detects the electromagnetic radiation.

The electromagnetic radiation emitted from the emitter may be infrared, visible or ultraviolet radiation. Suitably, radiation in the range 0.95 µm to 0.35 µm is used. More suitably, the radiation is in the infrared range. In particular, infrared radiation with a wavelength of 0.88 µm has been found to be useful.

Suitably, the emitter is selected from the group consisting of light emitting diode, laser, incandescent lamp, electroluminescent and fluorescent light sources. Suitably, the emitter emits infra red radiation. In one embodiment, the emitter may include a filter, suitably an optical filter and preferably a polarising filter (particularly if the emitter is an incandescent source) in order to select a particular wavelength, a narrow range or ranges of wavelength. Several advantages may be obtained by selecting a particular wavelength or range/ranges of wavelength, for example a given range of wavelengths may be especially sensitive to a particular drug/propellant combination. Alternatively, one 'sensitive' range and one 'insensitive' range may be selected—in this case the ratio of the two or more wavelengths reaching the detector would be used to detect the drug, thus making the sensor less prone to errors caused by an overall reduction in intensity due to contamination of the optical path.

Suitably, the detector is selected from the group consisting of photodiode, phototransistor, light-dependent resistor and bolometer. Preferably, the detector detects infra red radiation. In one embodiment, the detector additionally comprises a filter, suitably an optical filter and preferably a polarising filter. The use of a filter will enable the wavelength/wavelengths detectable by the detector to be pre-determined giving advantages similar to those described for using a filter with the emitter, for example, the detector could be made sensitive only to the wavelengths chosen for the emitter so the detector could be less sensitive to extraneous light sources, such as room light/sun light. In a further embodiment, the detector is associated with an amplifier, since the output from the detector can be very small (of the order of micro Amps). Suitably, the amplifier is positioned as closed to the detector as possible to avoid amplifying any extraneous noise e.g. any electrical noise picked up in the connecting wires. In one particular embodiment, the amplifier is integrated with the detector, for example the detector and amplifier are positioned on the same integrated circuit or "chip".

The detector may detect either an increase or decrease in radiation, compared to the amount of radiation emitted by the emitter. The increase or decrease may be due to interference of radiation reaching the detector by the medicament release.

In one aspect, the interference is due to absorption of radiation by the medicament release.

In another aspect, the interference is due to scattering of radiation by the medicament release.

In a further aspect, the interference is due to reflection of radiation by the medicament release.

In a yet further aspect, the interference is due to refraction of radiation by the medicament release.

In a still further aspect, the interference is due to diffraction of radiation by the medicament release.

In one aspect, the interference results in a decrease in the amount of radiation reaching the detector, for example due to absorption, scattering, refraction or diffraction, resulting in a decrease in the output signal. Alternatively, the amount of radiation reaching the detector may be maintained at a constant level by increasing the input level to the emitter. For example, an electronic feedback circuit that increases the current flowing through the emitter in order to maintain a constant flux at the detector may be used, resulting in an increase in the current supplied to the emitter as the medicament is released.

In a second aspect, the interference results in an increase in the amount of radiation reaching the detector, for example due to reflection by the medicament release, resulting in an increase in the output signal. Alternatively, the amount of radiation reaching the detector may be maintained at a constant level by decreasing the input level to the emitter. For example, an electronic feedback circuit that decreases the current flowing through the emitter in order to maintain a constant flux at the detector may be used, resulting in a decrease in the current supplied to the emitter as the medicament is released. In one aspect, the emitter emits radiation of more than one wavelength and the detector detects radiation of more than one wavelength.

Preferably, the first sensor can quantify the concentration of medicament within the medicament release by measuring radiation at more than one wavelength. These data can be processed, for example by a microprocessor, and compared against standardised data for a specified medicament to determine the concentration in the emission. For example, a first wavelength is used as a control to calibrate the system response. Suitably, this wavelength is not affected by the medicament release. A second wavelength is affected by the medicament release, for example due to interference of the radiation by the medicament release. The ratio of the amount of radiation of the first wavelength to the amount of radiation of the second wavelength arriving at the detector will depend on the concentration of medicament in the medicament release.

In another aspect, the medicament dispenser additionally comprises a second sensor (suitably having an emitter and a detector) for detecting a medicament release. Suitably, the second sensor is positioned such that the medicament release passes the second sensor subsequent to passing the first sensor. The presence of a second sensor may be used to increase confidence in the detection of the medicament release, for example for a detection to be considered valid, both sensors must be triggered. For example, a single sensor may be "triggered" by a foreign body interrupting the radiation path, but in this case the second sensor would not be "triggered"; thus the detection would not be considered valid and a dose not shown as given. Furthermore, the time lapse between triggering of the first sensor and triggering of the second sensor may be used to determine whether a detection is valid, i.e. the second sensor must be triggered within a specified time of the triggering of the first sensor.

In a further aspect, the medicament dispenser additionally comprises a third sensor. Suitably, the third sensor is sensitive to parameters selected from the group consisting of electro magnetic radiation, magnetic field, light, motion, temperature, pressure, sound, oxygen concentration, carbon dioxide concentration and moisture. Preferably the third sensor responds to actuation of the dispenser.

In one aspect, the first and/or second sensor is integral with the outlet, for example moulded into the outlet or is attached thereto. In a second aspect, the first and/or second sensor is reversibly attachable to the outlet and may be transferred from one outlet to another.

In another aspect, the third sensor is integral with the housing, for example moulded into the housing or attached hereto. Alternatively, the third sensor is reversible attachable to the housing.

The dose counter is associated electronically with the sensor(s), such that when the detector detects medicament release in the outlet, a signal is sent to the dose counter to record that a dose has been dispensed. In one aspect, the dose counter comprises a microprocessor. Suitably, the microprocessor performs operations on the data from the first sensor and produces a signal output relating to the data or the outcome of an operation on the data. Preferably, the microprocessor performs operations on the data from the second or third sensor and produces a signal output relating to the data or the outcome of an operation on the data. More preferably, the data from the second and/or third sensor is processed by the microprocessor to validate data from the first sensor.

In one aspect, the dose counter additionally comprises a visual display unit for display of the data. Preferably, the visual display unit displays the number of doses of medicament used or remaining within the container. Preferably the doses are displayed numerically, by a series of coloured lights or by a monochrome bargraph.

Suitably, the dose counter is reversibly attachable to the housing.

In one embodiment, the first and/or second sensors are located on the dose counter (either integral therewith or detachable therefrom).

In a further aspect, the medicament dispenser additionally comprises one or more optical wave guides located within the housing. Suitably the one or more optical wave guide is composed of an organic polymeric or inorganic glass fibre material.

Suitably, the medicament dispenser comprises two optical wave guides per sensor, i.e. one associated with the emitter and the other associated with the detector. A first optical wave guide channels radiation from the emitter to the outlet and a second optical wave guide channels radiation from the outlet to the detector.

Alternatively, the medicament dispenser comprises one optical wave guide per sensor, which may be associated with either the emitter or the detector.

In an alternative embodiment the emitter and detector may be located on the same side of the outlet, the radiation emitted from the emitter being reflected back to the detector by a reflective surface on the opposite side of the outlet. The emitter and detector may be separate components or may be integrated into a single component. The reflective surface may be the surface of the outlet or may be an additional component attached thereto. When the medicament dispenser is actuated, the medicament release causes a back-scattering of the signal off the particles/droplets in the plume spray, resulting in a reduction in the signal received by the detector.

In another aspect, the sensor is controlled by a digital or computational semiconductor device. Suitably, the digital or computational semiconductor device energises the sensor and associated electronic components to detect and respond to a medicament release every 10 to 100 ms. Preferably, the digital or computational semiconductor device energises the sensor and associated electronic components every 40 ms.

In one aspect, the sensor and associated electronic components are energised for 5 to 30 μs. Preferably, the sensor and associated electronic components are energised for 15 μs.

In a further aspect, the digital or computational semiconductor device returns the sensor to low power mode after energising the sensor. Preferably, the digital or computational semiconductor device returns to low power mode after the sensor has been de-energised.

In one aspect, the medicament container is an aerosol container. Preferably, the aerosol container comprises a suspension of a medicament in a propellant; in one embodiment, the propellant comprises liquefied HFA134a, HFA-227, or carbon dioxide; in an alternative embodiment, the propellant comprises a mixture of one or more of liquefied HFA134a, HFA-227, or carbon dioxide. Alternatively, the aerosol container comprises a solution of a medicament in a solvent.

In a further aspect, the medicament container is a dry-powder container. Preferably the dry-powder container comprises medicament and optionally excipient in dry-powder form.

Medicament dispensers according to the invention may be actuated manually by the patient. Alternatively, the dispenser is actuated on application of mechanical or non-mechanical energy to a coupling element, for example one or more shape memory alloy (SMA) wires, for example a medicament dispenser as disclosed in WO01/41849, which is incorporated herein in its entirety by reference. Alternatively, the dispenser is actuated by the application of mechanical or non-mechanical energy to a drive means, for example as described in UK Patent Application No. 0114175.3, which is incorporated herein in its entirety by reference.

The sensors of the present invention provide significant advantages for medicament dispensers which are actuated by the application of non-mechanical energy to a SMA coupling element, such advantages including: (i) preventing overheating of the SMA wires by shutting off the power as soon as they have contracted (heating the wires beyond this point does not result in any further contraction but may damage their microstructure, (ii) reducing or eliminating damage to the SMA wires, by preventing the wires driving against a hard stop by switching off the power as soon as the drug is released, (iii) saving energy by reducing the SMA drive pulse to a minimum by shutting the power off as soon as the drug is released thus preventing the wires being heated for longer than necessary, and (iv) giving confirmation of device actuation.

For example, the control electronics could be configured to:

(i) switch off the drive to the SMA wires as soon as the sensor detects the drug. This would rely on the valve staying open long enough to allow complete release of the dose after power to wires was switched off;

(ii) start a timer at the start of the medicament release and then switch off the power to the SMA wires at a pre-set time thereafter;

(iii) wait until the sensor detects completion of medicament release and then switch off the power to the SMA wires;

(iv) wait until the sensor detects a particular point in the drug profile (such as the peak) and then switch off the power to the SMA wires immediately or after a pre-set time.

Preferably, the medicament is selected from the group consisting of albuterol, salmeterol, fluticasone propionate, beclomethasone dipropionate, salts or solvates thereof and any mixtures thereof.

In one aspect, the outlet comprises a mouthpiece for inhalation therethrough.

In another aspect, the medicament dispenser additionally comprises a communicator for communication to enable transfer of data from the dose counter to an electronic data management system. Preferably, data from the dose counter are transferable onto a local data management system.

In one aspect, the medicament dispenser additionally comprises a communicator for wireless communication with a gateway to a network computer system to enable transfer of data between the network computer system and the electronic data management system.

In another aspect of the present invention there is provided the use of a medical dispenser according to any of the preceding claims to dispense medicament to a patient.

In a further aspect of the present invention there is provided a housing for receipt of a medicament container, the housing comprising (i) an outlet for dispensing medicament therethrough; and (ii) an electronic dose counter associated therewith; wherein the dose counter comprises a sensor for directly detecting a medicament release dispensible through the outlet.

In another aspect of the present invention there is provided a housing for receipt of a medicament container, the housing comprising (i) an outlet for dispensing medicament therethrough; and a first and second strand of optical wave guide associated therewith.

In a yet further aspect of the invention, there is provided a dose counter comprising a sensor for detecting a medicament release.

In yet another aspect of the present invention there is provided a kit of parts comprising a housing according to the present invention and an electronic dose counter comprising a sensor for directly detecting a medicament release.

Energy may be conserved by a variety of means to enable the device to operate for longer on a given source of energy, such as a battery. Energy conservation or saving methods have additional advantages in terms of reducing the size requirements of the power source (e.g. battery) and thus the weight and portability of the inhalation device.

According to another aspect herein, a variety of energy saving methods are is available which generally involve reducing power consumption. One such method is to use a clock or timer circuit to switch the power on and off at regular or predetermined intervals. In another method the system can selectively switch on/off specific electronic devices, such as visual display units, electronic agitators or sensors, in order to power these devices only when they are required to perform a particular sequence of events. Thus different electronic devices may be switched on and off at varying intervals and for varying periods under control of the system. Sensors, for example, may be energised at predetermined intervals (e.g. every 100 milliseconds) and for predetermined periods (e.g. 50 microseconds) thereby conserving power but being active long enough to detect specific stimuli, such as inhalation by the patient. Similarly, emitter-detector pairs may be controlled such that emitters are activated to pulse stimuli (e.g. electro magnetic radiation or sound) at predetermined intervals to appropriate detectors which are only energised to sense these stimuli at corresponding intervals. The power sequencing system may also respond to a sensor, such as a motion or breath sensor, which is activated on use of the device.

Low power or "micropower" components should be used within the electronics where possible and if a high power device is required for a particular function this should be put into a low power standby mode or switched off when not required. Similar considerations apply in the selection of transducers. Operation at low voltage is desirable since power dissipation generally increases with voltage.

For low power digital applications complementary metal oxide semi-conductor (CMOS) devices are generally preferred and these may be specially selected by screening for low quiescent currents. Clock speeds of processors and other logic circuits should be reduced to the minimum required for computational throughput as power consumption increases with frequency. Supply voltages should also be kept at minimal values consistent with reliable operation because power dissipation in charging internal capacitance's during switching is proportional to the square of the voltage. Where possible, supply voltages should be approximately the same throughout the circuit to prevent current flowing through input protection circuits. Logic inputs should not be left floating and circuits should be arranged so that power consumption is minimised in the most usual logic output state. Slow logic transitions are undesirable because they can result in relatively large class-A currents flowing. Resistors may be incorporated in the power supply to individual devices in order to minimise current in the event of failure.

In some control applications, devices that switch between on and off states are preferred to those that allow analog (e.g. linear) control because less power is dissipated in low resistance on states and low current off states. Where linear components are used (e.g. certain types of voltage regulators) then types with low quiescent currents should be selected. In some circuit configurations it is preferable to use appropriate reactive components (i.e. inductors and capacitors) to reduce power dissipation in resistive components.

According to another aspect herein, emitter-detector pairs, including those described in the present invention based upon the emission and detection of electro magnetic radiation, may be used as a means of detection in inhalation devices. Other forms of emitter and detector pairs can also be used to sense movement within the inhalation device such as those based upon sound, temperature, and pressure. Thus, for example, actuation of the device in the form of movement of the canister might be registered by interfering with a high frequency sound emanating from an emitter and sensed by an appropriate detector. Similar detection methods could be based upon the emission and detection of a pressure wave (e.g. in the form of an acoustic wave) or of a heat wave. Such emitter-detector pairs can be arranged to detect movement within the inhalation device; typical examples include movement of the mouthpiece, loading, transport and preparation of medicament (e.g. removal of cover strip in a blister pack prior to medicament release) and sample metering (e.g. filling of metering chamber with medicament powder, aerosol or liquid).

The position and relative configuration of the emitter-detector pair could also be varied to optimise performance and sensitivity. Thus, for example, the detector might be positioned diametrically opposite, or at any point within a 360° arc around, the emitter for receipt of the appropriate stimulus (e.g. electro magnetic radiation, sound etc.). Alternatively the detector might be attached to the canister, such that an appropriate stimulus was only received when the emitter-detector pair were aligned.

BRIEF DESCRIPTION OF THE DRAWINGS

FIG. 7 shows a plan sketch view of an outlet having wherein a reflective surface is used to return direct the infra red radiation from the emitter back to the detector.

DETAILED DESCRIPTION OF DRAWINGS

Figure 1:
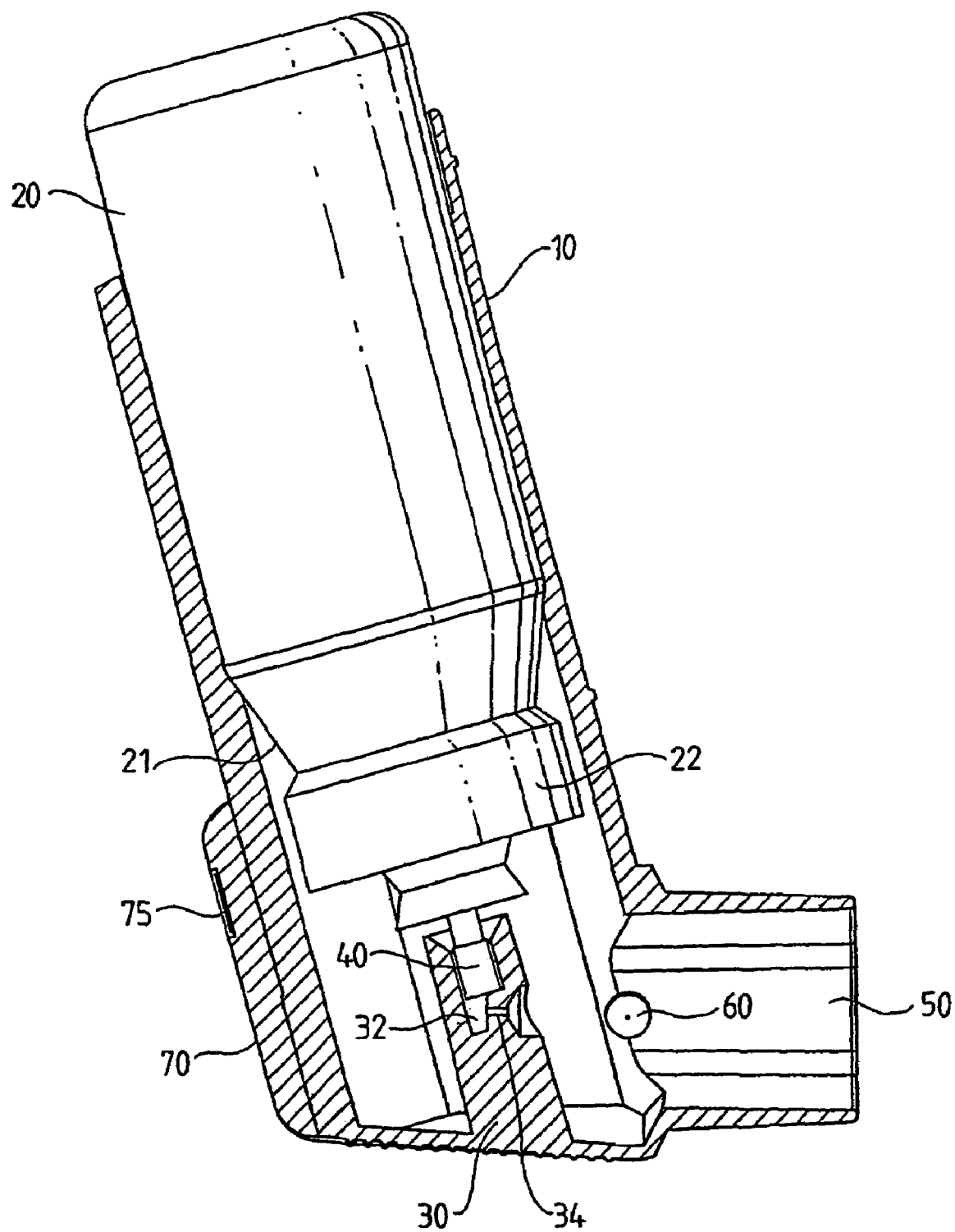
FIG. 1 shows a cross-sectional perspective of a MDI having a single sensor.

For the sake of brevity, each drawing depicts a sensor comprising an emitter/detector pair which emit and are responsive to infra red radiation. It should be understood that other forms of sensors, detailed herein, could equally be described in the drawings and used in the present invention. Furthermore, the drawings could equally apply to a sensor comprising only of a detector and lacking the corresponding emitter. As shown in the cross-sectional perspective of FIG. 1, the aerosol canister 20 is located in the housing 10 so that one end protrudes from its open top, the canister being positioned such that the neck 21 and valve ferrule 22 are enclosed within housing 10. Spacer ribs (not shown) may be provided inside the housing to hold the external surface of the canister 20 spaced from the internal surface of the housing 10. A support 30 is provided at the lower end of the housing 10 and has a passage 32 in which the valve stem 40 of the aerosol canister 20 can be located and supported. A second passage 34 is provided in the support 30 and is directed towards the interior of the outlet 50. An emitter 60 is located on outlet 50. Emitter 60 emits an infra red beam (not shown) across outlet 50 onto a detector (not shown) attached to the other side of outlet 50. The emitter 60 may emit a continuous beam of infra red radiation or may emit a pulsed beam at varying intervals and for varying duration. The emitter 60 is under the control of a microprocessor within dose counter unit 70. The detector (not shown) is responsive to change in infra red radiation and generates a signal readable by the microprocessor. When the level of energy falls below a predetermined threshold for a predetermined period (calibrated to respond to an emission of medicament released from canister 20) the microprocessor updates the display on the visual display unit 75 indicating the doses used or remaining within the canister.

The detector is calibrated to respond to an emission of medicament released from canister 20. The signal results in a change in the display on the visual display unit 75 indicating the doses used or remaining within the canister.

Thus, when the parts are in the positions shown in FIG. 1, the protruding portion of the aerosol canister 20 can be depressed to move the canister relative to the valve stem 40 to open the valve and a dose of medicament contained in the canister 20 will be discharged as a medicament release through passage 34 and into the outlet 50 from which it can be inhaled by a patient. One dose will be released from the aerosol canister each time it is fully depressed. The medicament release will interfere with the beam of infra red radiation from emitter 60 resulting in a reduction in radiation reaching the detector. The visual display unit 75 will be updated to display the number of doses used or remaining within the canister 20. This display may consist of a numerical read out, giving the precise number of doses used or remaining. Alternatively, the display may be indicative of the number of doses used or remaining, based upon a series of coloured lights (e.g. green, orange, red) representing an estimated range of the number of doses used or remaining.

Figure 2:
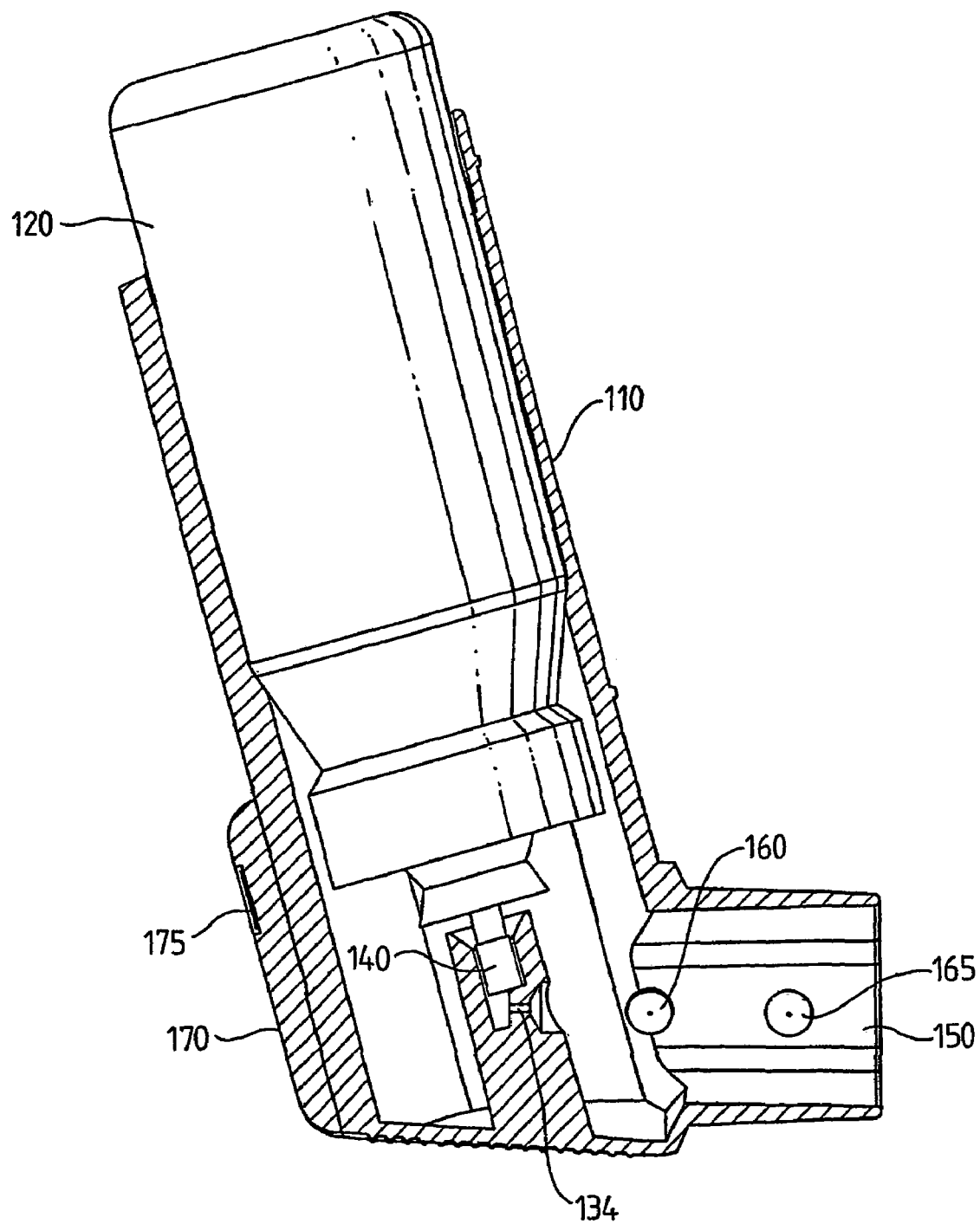
FIG. 2 shows a cross-sectional perspective of a MDI having two sensors.

FIG. 2 is another cross-sectional perspective showing a second embodiment of the invention. Two emitters 160, 165 are attached to outlet 150 and emit infra red beams (not shown) onto their respective detectors (not shown) attached to the other side of outlet 150. The infra red beams may be emitted continuously or pulsed (e.g. at 40 millisecond intervals for 15 microseconds) across outlet 150.

A dose of medicament is dispensed from canister 120, by depressing and moving the canister relative to valve stem 140, to release a dose of medicament as a medicament release through passage 134 into outlet 150. The infra red beams emitted or pulsed from emitters 160 and 165 are broken by the emission from the canister 120, resulting in a reduction in radiation reaching their respective detectors (not shown). The two electronic signals from the detectors are processed by a microprocessor within the dose counter unit 170. This processing serves both to register that a single dose of medicament has been dispensed from the canister 120 and to validate that the response of each detector is not due to an error (e.g. resulting from dust or dirt in the outlet or on the detector surface). On validation by the processor, the number of doses remaining or used within the canister 120 is displayed on the visual display unit 175.

Figure 3A:
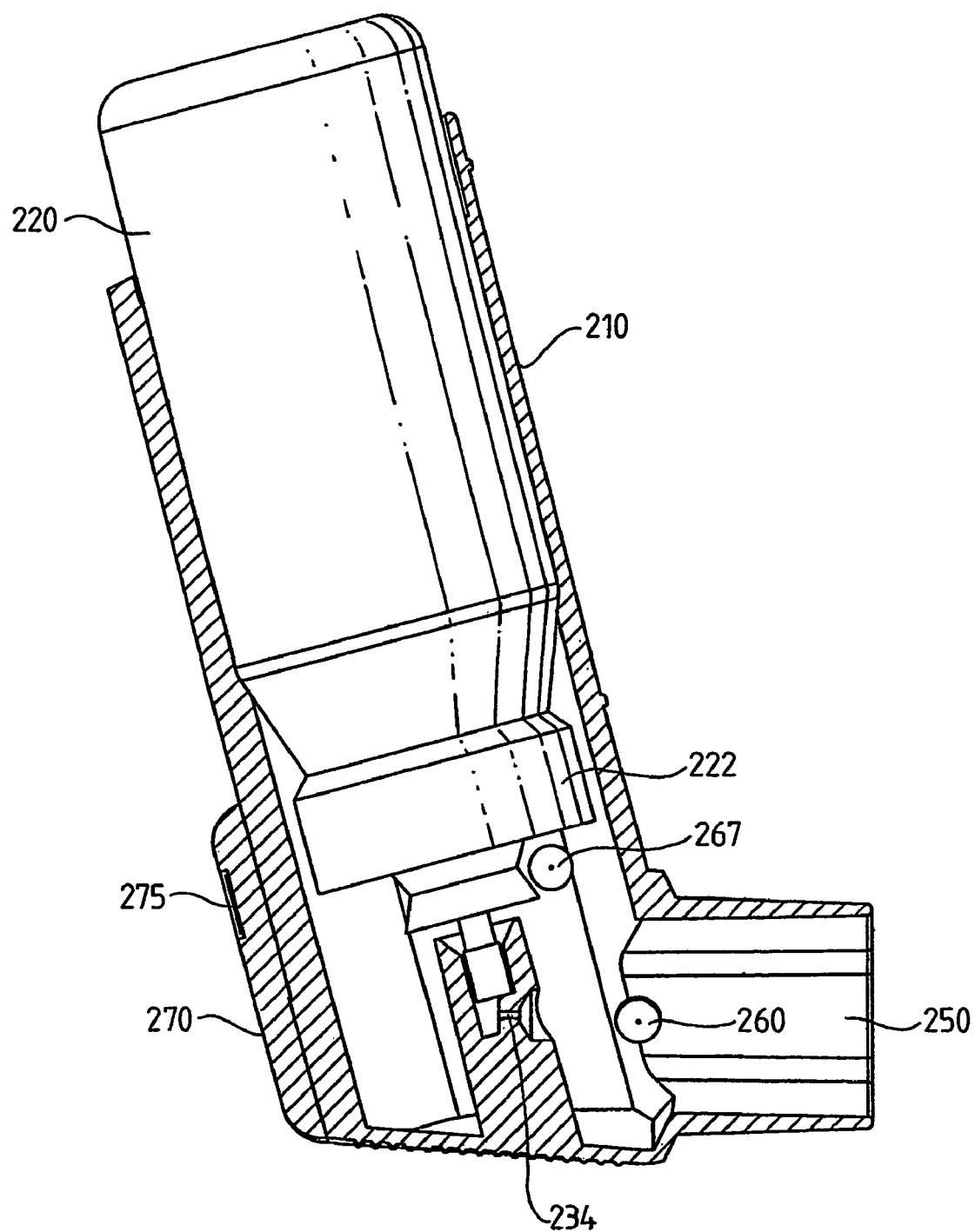
FIGS. 3a-d show a cross-sectional, side, front cross-sectional (along the line C-C of FIG. 3b) and rear perspective, respectively, of a MDI having two sensors.

Another embodiment of the present invention is shown in FIGS. 3*a*-*d*. The cross-sectional perspective diagram of FIG. 3*a* shows a medicament dispenser similar to that of the preceding Figures. Two emitters 260, 267 are attached to the housing 210 and emit a continuous or pulsed beam of infra red energy onto two detectors (not shown) positioned opposite each emitter and attached to the housing 210. On depression of canister 220 a dose of medicament is dispensed as a medicament release through passage 234 into outlet 250. The medicament release breaks the infra red beam emanating from emitter 260 which is sensed by the detector. The depression of the canister 220 also causes ferrule 222 to disrupt the infra red beam emitted from emitter 267, resulting in a reduction in radiation reaching the detector. A microprocessor within the dose counter unit 270 processes the signal from each detector to validate whether or not a single dose of medicament has been dispensed from the canister 220, validation requiring appropriate signals from each detector. If the processor validates that one dose has been emitted, the dose counter displays the number of doses remaining or used within the canister 220 on the visual display unit 275.

Figure 3B:
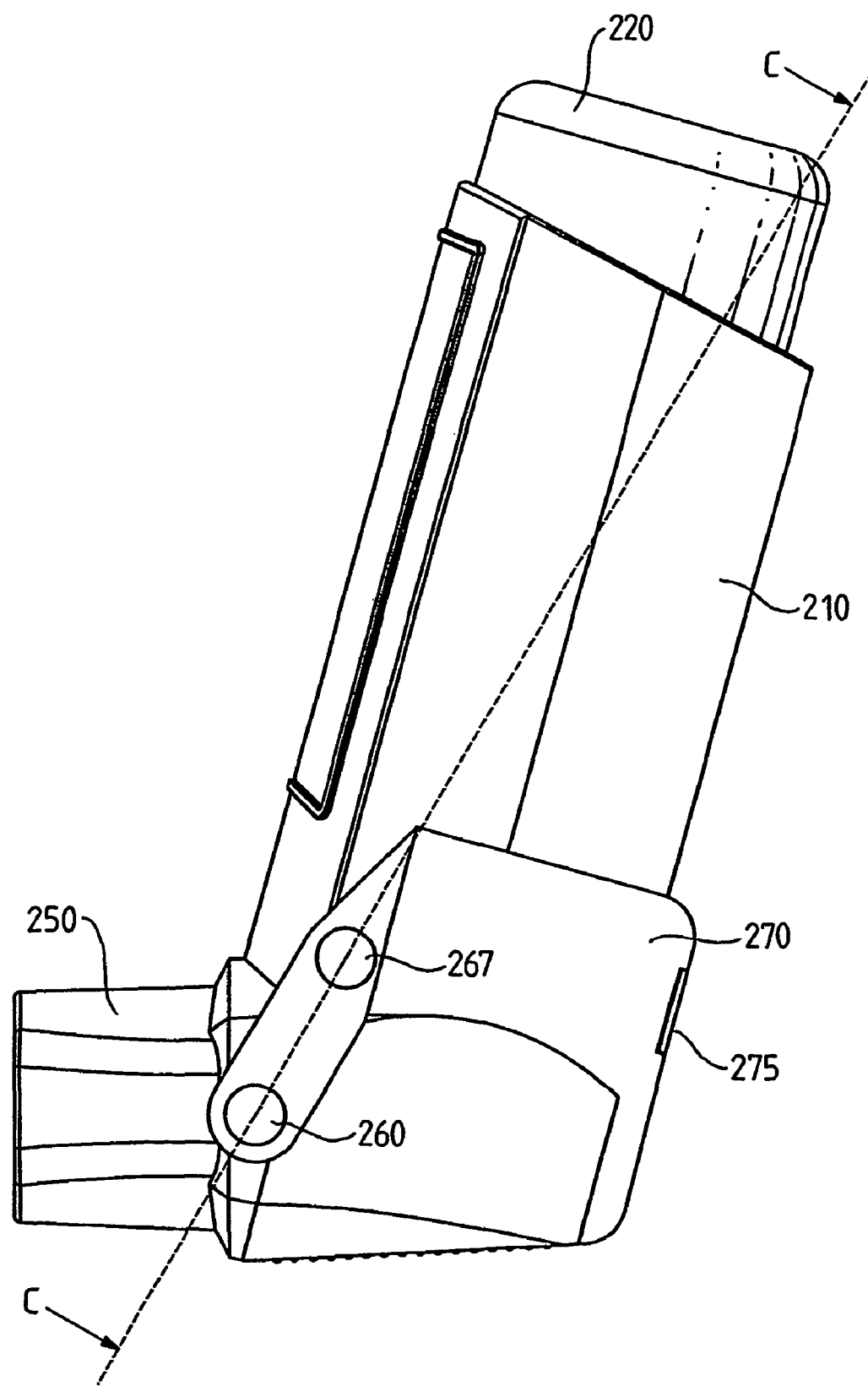

FIG. 3*b* shows a side elevation of the medicament dispenser of FIG. 3*a*. The dispenser comprises a housing 210 for receipt of aerosol container 220. Medicament within container 220 is dispensed through outlet 250 to the patient. Two emitters 260, 267 are located on the side of the housing and emit infra red radiation across the device as described above. The dose counter unit 270 and visual display unit 275 are attached to the housing.

Figure 3C:
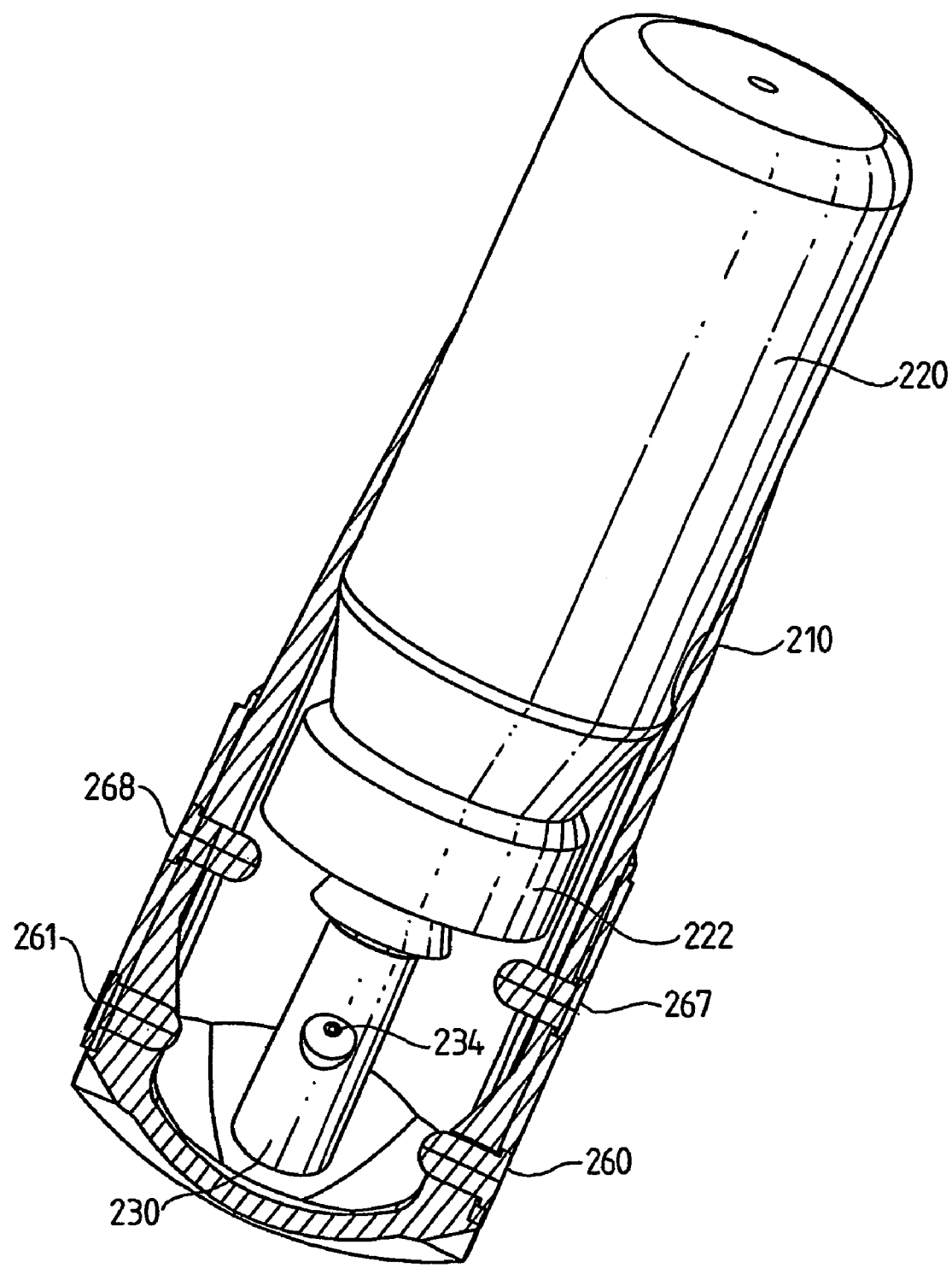

FIG. 3*c* is a cross-sectional view along the line C-C of FIG. 3*b*. The aerosol canister 220 is positioned within housing 210 such that the canister outlet (not shown) is received by support 230. When the dispenser is not in use, emitters 260 and 267 emit or pulse infra red radiation across the interior of the housing onto detectors 261 and 268, respectively. The detectors are calibrated to respond to a reduction in infra red radiation. On depression of canister 220 a dose of medicament in a propellant is released as a medicament release through passage 234 into outlet 250. The movement of ferrule 222 blocks the beam of infra red energy from emitter 267 and this blockage is sensed by detector 268 which sends a signal to the microprocessor within dose counter 270. Simultaneously, the release of medicament and propellant from passage 234 breaks the beam of infra red radiation from emitter 260 and results in detector 261 sending a signal to the microprocessor within the dose counter unit 270. Signals from both detectors 261 and 268 are processed by the microprocessor to validate whether a single dose of medicament has been dispensed. Signal validation results in a change in the number of doses displayed by the visual display unit (not shown).

Figure 3D:
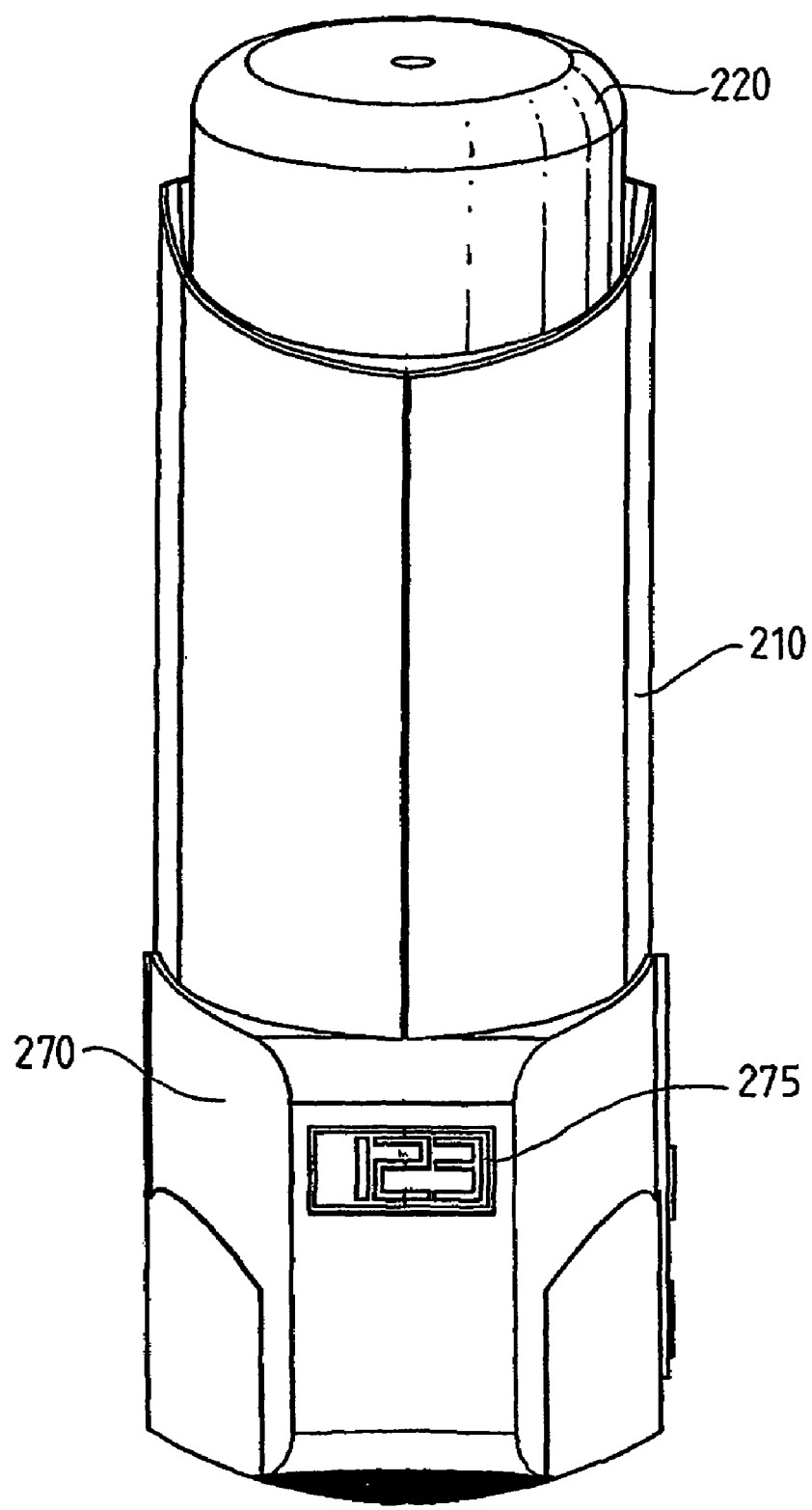

A rear perspective of the medicament dispenser of FIGS. 3*a*-*c* is shown in FIG. 3*d*. The key feature illustrated in this view is the visual display unit 275 on dose counter unit 270 indicating the number of doses used or remaining within the container 220.

Figure 4B:
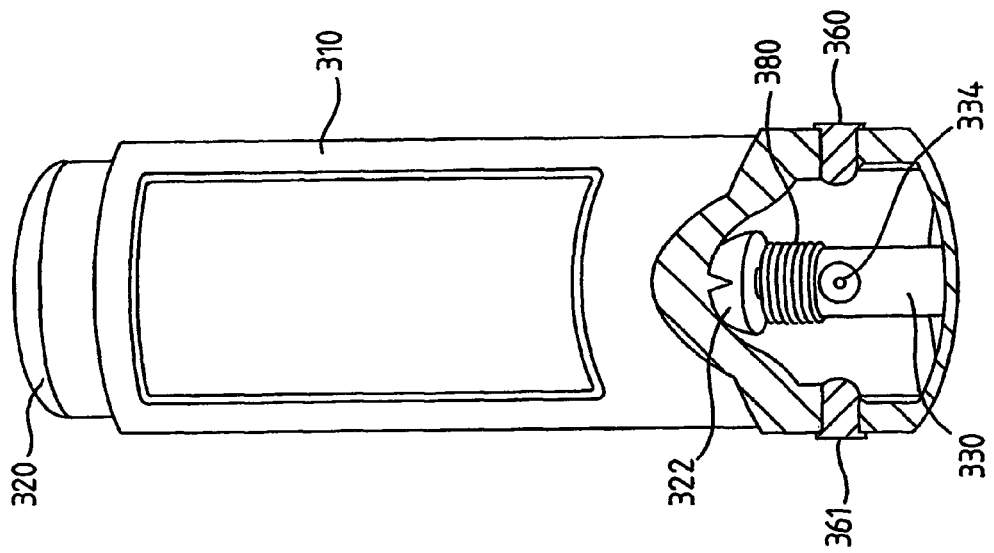
FIGS. 4a & b show side and front-sectional perspective (along the line A-A of FIG. 4a) of a MDI having two sensors.
Figure 4A:
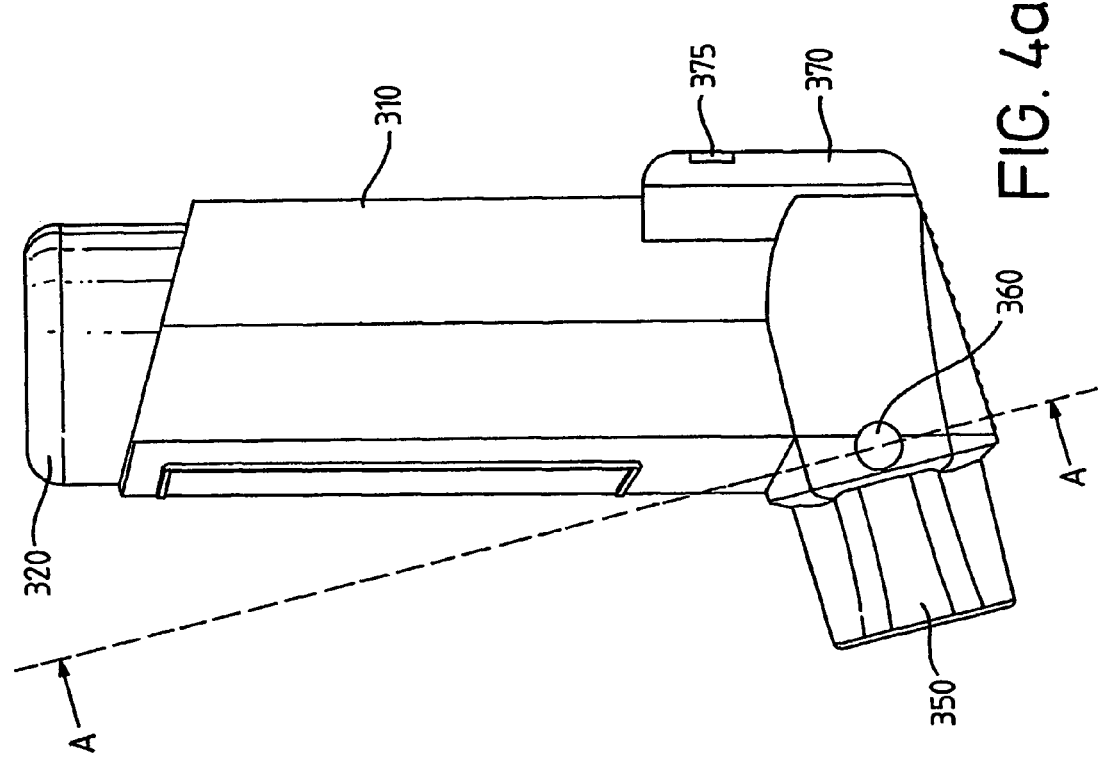

FIGS. 4*a* and 4*b* show another embodiment of the invention. The side perspective (FIG. 4*a*) illustrates a medicament dispenser comprising a housing 310 with outlet 350 and containing an aerosol canister 320. The dispenser has a dose counter 370 with visual display unit 375 for indicating the number of doses used or remaining within the canister 320. An infra red emitter 360 and detector 361 are positioned across the outlet 350 to detect a release of medicament in propellant from passage 334, as discussed above. As can be seen from FIG. 4b, a cut away section along the line A-A of FIG. 4a, an inductive coil 380 carrying a low electrical current is located on support 330. The inductive coil forms part of an inductive displacement transducer such that depression of canister 320 disturbs the magnetic field created by the flow of current in coil 380. Actuation of the device can therefore be detected as a change in the oscillating frequency of the circuit by the dose counter unit 370. Validation of actuation of the device is achieved by the microprocessor within the dose counter unit 370 is processing signals from both the infra red detector 361 and coil 380. If the processor confirms that actuation and medicament release has occurred then the number of doses used or remaining within the canister 320 is changed accordingly on the visual display unit 375.

Figure 5:
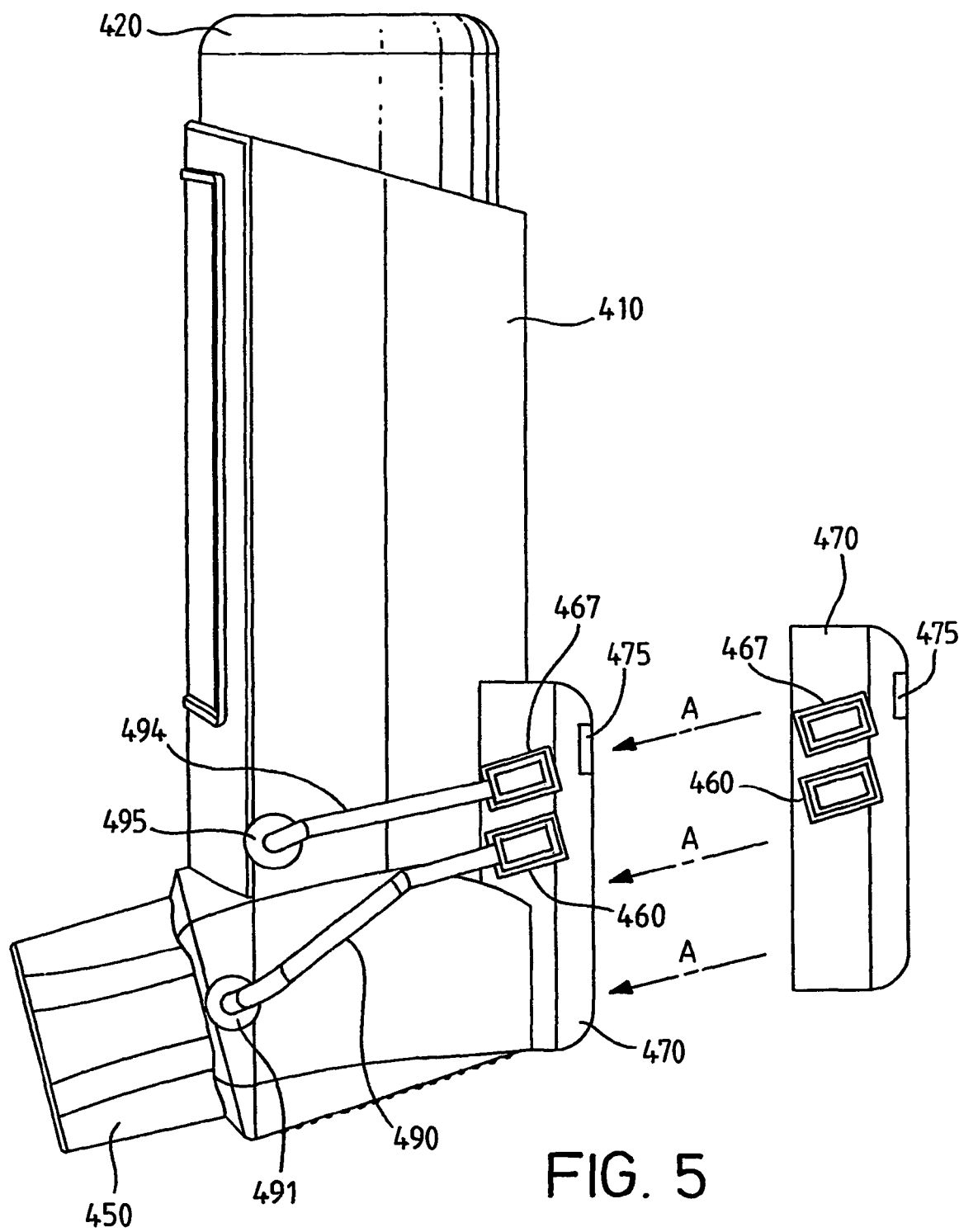
FIG. 5 is a schematic side perspective of a MDI comprising a detachable dose counter unit having two sensors.

FIG. 5 is a schematic diagram depicting a variant of the present invention. The medicament dispenser of FIG. 5 comprises a detachable dose counter unit 470 with emitters 460, 467 and detectors (not shown) attached thereto. The attachment of dose counter 470 to housing 410 is shown by arrows A in FIG. 5. The dispenser housing 410 is provided with light piping 490, 494 which is connectable at one end to the emitters 460, 467 on detachable dose counter unit 470. Another pair of light pipes (not shown) are attached to the housing 410 on the opposite side of the dispenser. The other ends 491, 495 of the light piping 490, 494 fit through the body of the housing 410 and are positioned within the housing in a similar manner to the emitters/detectors of FIGS. 3a-d. Thus two sets of light tubes are located on both sides of the dispenser and end on the internal surfaces of housing 410, being positioned on either side of the mouthpiece and below the container ferrule (not shown). Infra red radiation emitted or pulsed from emitter 460 will be transmitted through light tube 490 across the interior of outlet 450 and channelled by the corresponding light tube on the opposite side of the mouthpiece to the detector (not shown) on dose counter unit 475. Similarly, infra red radiation from emitter 467 will be channelled through light tube 494 across the interior of the housing, below the ferrule (not shown), and transmitted by the corresponding light tube on the opposite side of the housing 410 to the detector (not shown).

On actuation of the device, the release of medicament from the canister 420 will break the beam of infra red radiation transmitted across the interior of outlet 450 from emitter 460. This will result in a reduction in radiation being channelled through the corresponding light pipe to the detector (not shown), on dose indicator 470, and an output signal from the detector. Depression of the canister 420 will push the ferrule (not shown) across the path of the infra red light beam transmitted through and from light pipe 494. The reduction in energy being transferred through the corresponding light pipe on the opposite side of the housing 410 to the detector (not shown) will result in an output signal. The microprocessor within the dose unit 470 will validate these signals to ensure that one signal is not due to an artefact. If satisfied that a dose of medicament has been dispensed, the microprocessor will indicate a change in the number of doses used or remaining within the container 420.

Figure 6B:
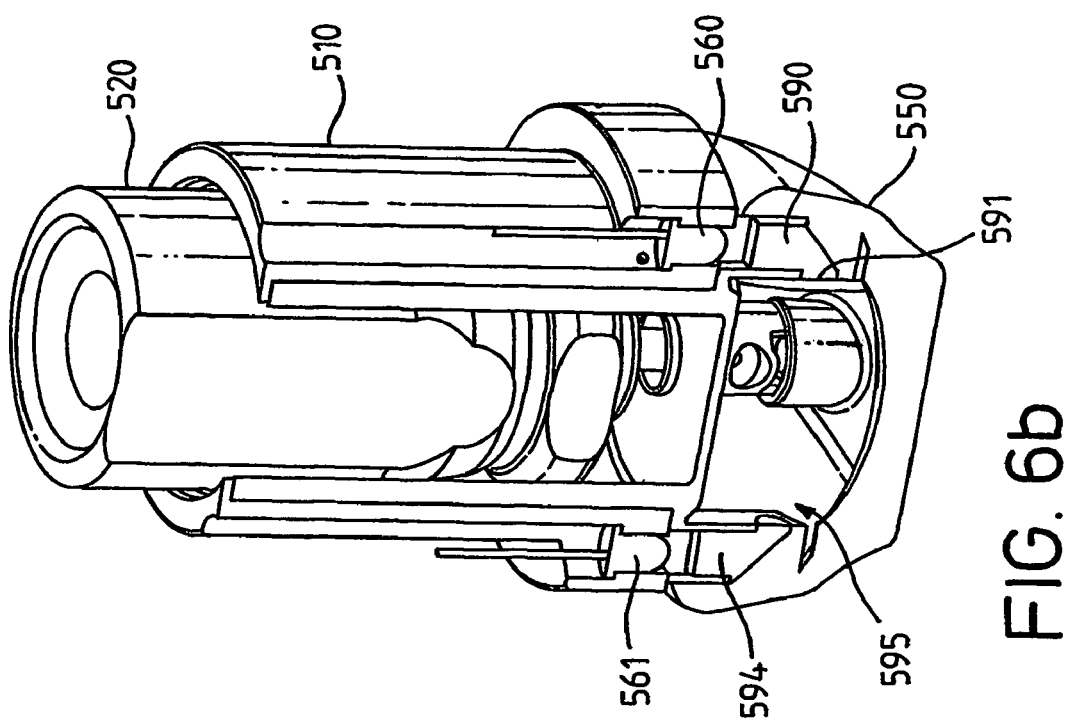
FIGS. 6a and 6b show front and front-sectional perspective (along line B-B of FIG. 6a) of a MDI having a rotatable outlet (mouthpiece).
Figure 6A:
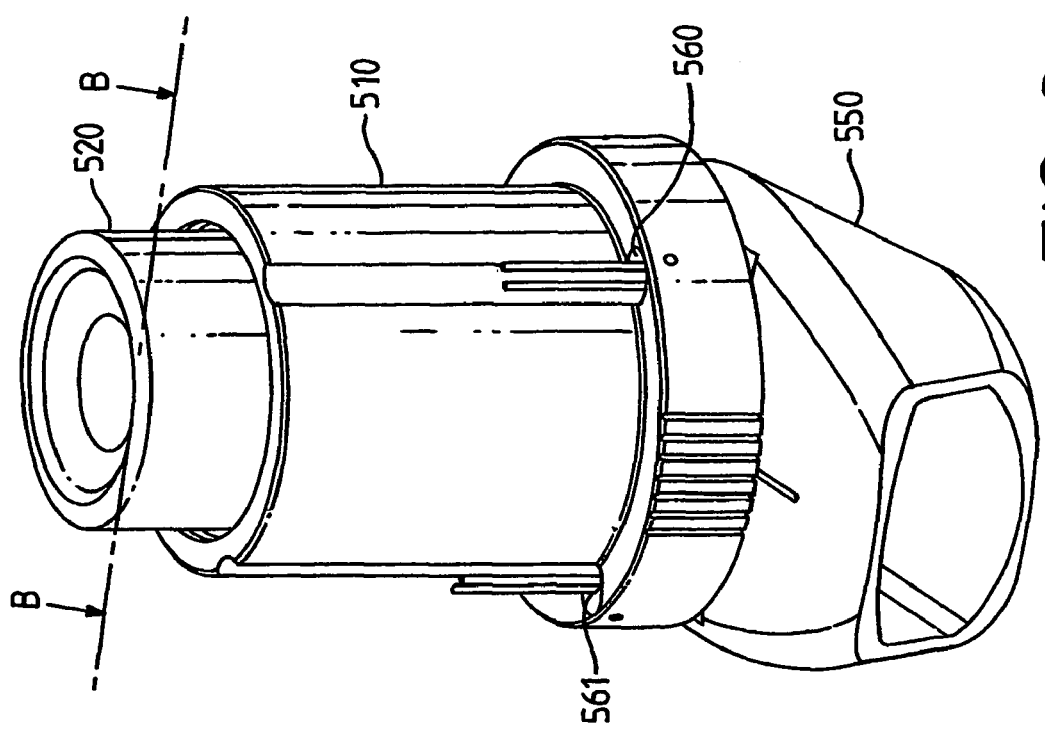

FIG. 6a shows a perspective view of a medicament dispenser of the invention and FIG. 6b shows a cross-sectional cut away view along the line B-B of FIG. 6a. The dispenser comprises a housing 510 for receipt of aerosol container 520. Medicament within container 520 is dispensed to the patient through outlet 550 rotatably attached to housing 510. An infra red emitter 560 and detector 561 with connecting wires attached are located on housing 510. Light piping 590, 594 is connectable at one end to emitter 560 and detector 561 respectively. The other ends 591, 595 of light piping 590, 594 fits through the body of the housing 510 and are positioned within the housing in a similar manner to the emitter/detector in FIG. 3a-3d. Infra red radiation emitted or pulsed from emitter 560 will be transmitted through light tube 590 across the interior of outlet 550 and channelled by the corresponding light tube 594 on the opposite side of the mouthpiece to the detector 561.

On actuation of the device, the release of medicament from the canister 520 will break the beam of infra red radiation transmitted across the interior of outlet 550 from emitter 560. This will result in a reduction in radiation being channelled through the corresponding light pipe 594 to the detector 561 and an output signal from the detector. The reduction in energy being transferred through the corresponding light pipe 594 on the opposite side of the housing 510 to the detector 561 will result in an output signal. The microprocessor within the dose counter (not shown) will validate this signal and if satisfied that a dose of medicament has been dispensed, the microprocessor will indicate a change in the number of doses used or remaining within the container 520.

FIGS. 7a shows a side perspective of a medicament dispenser of the invention comprising housing 610 with outlet 650 and containing an aerosol canister 620. The dispenser has a dose counter 670 with visual display unit 675 for indicating the number of doses used or remaining within the canister 620. FIGS. 7b and 7c are cross-sectional views along line D-D. A sensor component 665 comprising emitter and detector is located on the housing 610 above outlet 650 and has a clear optical path provided by hole 666 located on the centre line on the upper surface of the mouthpiece. The lower surface of outlet 650 is provided with a reflective surface 655. The infra red signal emitted from sensor 665 is reflected off the reflective surface 655 back to the detector part of sensor 665. During actuation of the device, a medicament release is released from passage 634. The particles/droplets in the medicament release cause a scattering of the infra red beam (FIG. 7c) thus causing a reduction of the signal reaching the detector portion of sensor 665. The microprocessor within the dose counter 670 will validate this signal and if satisfied that a dose of medicament has been dispensed, the microprocessor will indicate a change in the number of doses used or remaining within the container 620.

Figure 8:
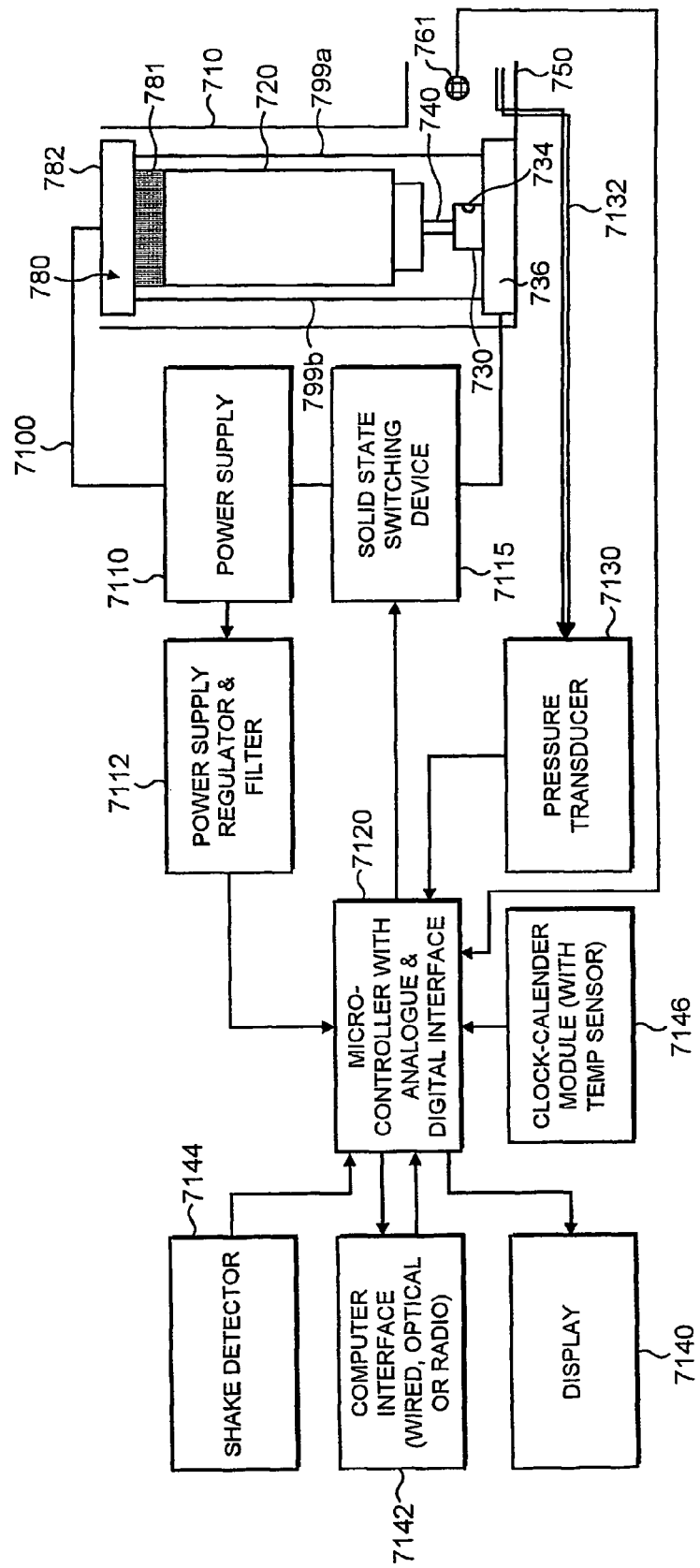
FIG. 8 shows a medicament dispenser and an associated system diagram.

FIG. 8 shows a schematic representation of a breath-operable medicament dispensing system. The system comprises a metered dose inhaler similar to that shown in more detail in FIG. 1 comprising tubular housing 710 having a dispensing outlet 750 in the form of a mouthpiece. Within the housing 710 sits aerosol container 720 which has a valve. Valve stem 740 is supported by valve support 730. Outlet passage 734 is provided in the support 730 to enable passage of dispensed dose to the dispensing outlet 750. An emitter 760 is located in outlet 750. An emitter (not shown) emits an infra red beam (not shown) across outlet 750 on to a detector 761 attached to the other side of outlet 750.

It may be seen that the upper part of the aerosol container 720 abuts container seat 780. The container seat 780 comprises an insulating portion 781 which directly contacts the aerosol container 720 and an upper conducting portion 782 (e.g. comprised of aluminium). It may also be seen that the valve support 730 connects with conducting valve seat 736. Plural shape memory alloy wires 799a, 799b connect the conducting portion 782 of the container seat 780 to the conducting valve seat 736. The plural wires 799a, 799b comprise a nickel-titanium alloy which contracts in response to electrical current flow therethrough. It may thus, be appreciated that on passage of electrical current through the plural wires 799a, 799b the container seat 780 and valve seat 736 will be drawn towards each other as the wires 799a, 799b contract. Actuation of the valve will result and a medicament release dispenser through outlet 750. The medicament release will interfere with the beam of infra red radiation from emitter (not shown) resulting in a reduction in radiation reaching the detector 761.

Control of electrical current flow to the container seat 780, valve seat 736 and wires 799a, 799b is achievable using the illustrated circuitry. Container seat 780 and valve seat 736 connect to actuation circuit 7100 which includes a power supply 7110 (e.g. a voltaic cell or battery of voltaic cells) and a switch 7115 in the form of a solid state switching device. The switch 7115 itself connects to control circuitry including micro-controller 7120 which has an analogue and digital interface. The power supply for the control circuitry is taken from the power supply 7110 for the wires 799a, 799b after suitable regulation and filtering 7112. The micro-controller 7120 itself connects with pressure transducer 7130 which has an input in the form of a pressure tube 7132 located within the dispensing outlet 750 of the inhaler housing 710.

It may be appreciated that current flow to the container seat 780, valve seat 736 and wires 799a, 799b, and hence actuation of the dispenser may be achievable as follows. The patient inhales through the outlet 750 resulting in a change in pressure within the housing 710 and pressure tube 7132. The change in pressure is detected by the pressure transducer 7130 which sends a signal to the micro-controller 7120. The micro-controller 7120, in turn sends a switching signal to the solid state switching device 7115 which results in closing of the actuation circuit and electrical current flow therethrough. The resulting contraction of the shape memory alloy wires 799a, 799b causes actuation of the dispenser and hence, dispensing of medicament to the inhaling patient. Interference of the infra red beam emitted by the emitter (not shown) is detected by the detector 761 and a signal sent to the micro-controller 7120 which can be configured to carry out one or more tasks. For example it may be configured to switch off the actuator circuit as soon as the medicament has been dispensed and to display an error message if the medicament is not dispensed.

It may also be seen in FIG. 8 that the micro-controller 7120 is connected to a display 7140 for display of information to the patient and also with a computer interface 7142 for exchange of data therewith. Communication with the computer interface 7142 may be via a wired, optical or radio communications link. The micro-controller 7120 is also connected to shake detector 7144 for use in detecting whether the container 720 is shaken prior to actuation of the dispenser and to a clock-calendar module 7146 including a temperature sensor. All circuitry and components thereof including the power supply 7110, display 7140, shake detector 7144, computer interface 7142 and clock-calendar module 7146 may be arranged to be present on the housing 710 such that the system is in the form of a discrete, hand-held device.

Whilst the present invention has been described in detail in respect of a metered dose inhaler it will be appreciated that identical sensors could be attached to a dry powder inhalation device in a similar fashion.

It may be appreciated that any of the parts of the dispenser which contact the chemical suspension may be coated with materials such as fluoropolymer materials which reduce the tendency of chemical to adhere thereto. Any movable parts may also have coatings applied thereto which enhance their desired movement characteristics. Frictional coatings may therefore be applied to enhance frictional contact and lubricants used to reduce frictional contact as necessary.

The medicament dispenser of the invention is suitable for dispensing medicament, particularly for the treatment of respiratory disorders such as asthma and chronic obstructive pulmonary disease. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulphonyl]ethyl]amino]ethyl-2 (3H) -benzothiazolone; adenosine 2a agonists, e.g. 2R,3R, 4S,5R)-2-[6-Amino-2-(1S -hydroxymeth-2-phenyl-ethylamino)-purin-9-yl]-5-(2-ethyl-2H-tetrazol-5-yl) -tetrahydro-furan-3,4-diol (e.g. as maleate); α4 integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant. Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It will be understood that the present disclosure is for the purpose of illustration only and the invention extends to modifications, variations and improvements thereto.

The invention claim is:

1. A medicament dispenser comprising:
   (i) a housing having an outlet;
   (ii) a medicament container locatable within said housing;
   (iii) an electronic dose counter associated with said outlet,
   wherein said dose counter includes a first sensor comprising an emitter and a detector for detecting a medicament release dispensable from said medicament container through said outlet, characterized in that the detector detects electromagnetic radiation in the infra red range, wherein the detector detects an increase in radiation compared to the amount of radiation emitted by the emitter
   wherein the increase in detected radiation is due to interference of radiation reaching the detector by the medicament release.

2. A medicament dispenser comprising:
   (i) a housing having an outlet;
   (ii) a medicament container locatable within said housing;
   (iii) an electronic dose counter associated with said outlet,
   wherein said dose counter includes a first sensor comprising an emitter and a detector for detecting a medicament release dispensable from said medicament container through said outlet, characterized in that the detector detects electromagnetic radiation in the infra red range, wherein the detector detects an increase in radiation compared to the amount of radiation emitted by the emitter, and
   wherein the increase in detected radiation is due to interference of radiation reaching the detector by the medicament release, and wherein the interference is due to absorption of radiation by the medicament release.

3. A medicament dispenser according claim 1, wherein the interference is due to scattering of radiation by the medicament release.

4. A medicament dispenser comprising:
   (i) a housing having an outlet;
   (ii) a medicament container locatable within said housing;
   (iii) an electronic dose counter associated with said outlet,
   wherein said dose counter includes a first sensor comprising an emitter and a detector for detecting a medicament release dispensable from said medicament container through said outlet, characterized in that the detector detects electromagnetic radiation in the infra red range, wherein the detector detects an increase in radiation compared to the amount of radiation emitted by the emitter, and
   wherein the increase in detected radiation is due to interference of radiation reaching the detector by the medicament release, and wherein the interference is due to reflection of radiation by the medicament release.

5. A medicament dispenser according claim 1, wherein the interference is due to refraction of radiation by the medicament release.

6. A medicament dispenser comprising:
   (i) a housing having an outlet;
   (ii) a medicament container locatable within said housing;
   (iii) an electronic dose counter associated with said outlet,
   wherein said dose counter includes a first sensor comprising an emitter and a detector for detecting a medicament release dispensable from said medicament container through said outlet, characterized in that the detector detects electromagnetic radiation in the infra red range, wherein the detector detects an increase in radiation compared to the amount of radiation emitted by the emitter, and
   wherein the increase in detected radiation is due to interference of radiation reaching the detector by the medicament release, and, wherein the interference is due to diffraction of radiation by the medicament release.

7. A metered dose inhaler for dispensing metered doses of medicament comprising:
   (i) a housing having an outlet;
   (ii) an aerosol container locatable within said housing, wherein the container;
      (a) contains a plurality of metered doses of medicament, and
      (b) has a dispensing means actuable to cause, in use, dispensing of a
      metered dose of the medicament from the container through the outlet;
   characterized by the inhaler further comprising;
   (iii) an electronic dose counter associated with said outlet, which comprises;
   a sensor for directly detecting a metered dose dispensed from said container through said outlet, said sensor comprising an emitter to emit electromagnetic radiation and a detector to detect the electromagnetic radiation emitted by the emitter, the emitter being arranged to emit the electromagnetic radiation such that it is interfered with by a metered dose of the medicament being dispensd from the container through the outlet whereby the sensor is able to detect said dispensing of the metered medicament dose, and
   a visual display unit for displaying the number of metered doses of medicament used or remaining within the container in response to the sensor detecting dispensing of a metered medicament does, and
   wherein the amount of radiation reaching the detector is maintained at a constant level by using an electronic feedback circuit to alter the level of radiation emitted by the emitter.

8. A medicament dispenser comprising:
   (i) a housing having an outlet;
   (ii) a medicament container locatable within said housing;
   (iii) an electronic dose counter associated with said outlet,
   wherein said dose counter includes a first sensor comprising an emitter and a detector for detecting a medicament release dispensable from said medicament container through said outlet, characterized in that the detector detects electromagnetic radiation in the infra red range, wherein the first sensor further comprises a reflector to reflect radiation from the emitter to the detector.

9. A medicament dispenser comprising:
   (i) a housing having an outlet;
   (ii) a medicament container locatable within said housing;
   (iii) an electronic dose counter associated with said outlet,
   wherein said dose counter includes a first sensor comprising an emitter and a detector for detecting a medicament release dispensable from said medicament container through said outlet, characterized in that the detector detects electromagnetic radiation in the infra red range, and wherein the emitter emits radiation of more than one wavelength and the detector detects radiation of more than one wavelength, and wherein the first sensor quantifies the concentration of medicament with the medicament release by measuring radiation at more than one wavelength.

10. A metered dose inhaler for dispensing metered doses of medicament comprising:
(i) a housing having an outlet;
(ii) an aerosol container locatable within said housing, wherein the container;
(a) contains a plurality of metered doses of medicament, and
(b) has a dispensing means actuable to cause, in use, dispensing of a
metered dose of the medicament from the container through the outlet;
characterized by the inhaler further comprising:
(iii) an electronic dose counter associated with said outlet, which comprises:
a sensor for directly detecting a metered dose dispensed from said container through said outlet, said sensor comprising
an emitter to emit electromagnetic radiation and a detector to detect the electromagnetic radiation emitted by the emitter,
the emitter being arranged to emit the electromagnetic radiation such that it is interfered with by a metered dose of the medicament being dispensd from the container through the outlet whereby the sensor is able to detect said dispensing of the metered medicament dose, and
a visual display unit for displaying the number of metered doses of medicament used or remaining within the container in response to the sensor detecting dispensing of a metered medicament dose,
wherein the metered dose inhaler additionally comprises a second sensor for detecting a medicament release and wherein the second sensor comprises an emitter and a detector.

11. A metered dose inhaler for dispensing metered doses of medicament comprising:
(i) a housing having an outlet;
(ii) an aerosol container locatable within said housing, wherein the container;
(a) contains a plurality of metered doses of medicament, and
(b) has a dispensing means actuable to cause, in use, dispensing of a metered dose of the medicament from the container through the outlet;
characterized by the inhaler further comprising:
(iii) an electronic dose counter associated with said outlet, which comprises:
a sensor for directly detecting a metered dose dispensed from said container through said outlet, said sensor comprising an emitter to emit electromagnetic radiation and a detector to detect the electromagnetic radiation emitted by the emitter, the emitter being arranged to emit the electromagnetic radiation such that it is interfered with by a metered dose of the medicament being dispensd from the container through the outlet whereby the sensor is able to detect said dispensing of the metered medicament dose, and
a visual display unit for displaying the number of metered doses of medicament used or remaining within the container in response to the sensor detecting dispensing of a metered medicament dose,
wherein the metered dose inhaler additionally comprises a second sensor for detecting a medicament release and
wherein the medicament release passes the second sensor subsequent to passing the first sensor.

12. A metered dose inhaler according to claim 10, further comprising a third sensor.

13. A metered dose inhaler according to claim 12, wherein the third sensor is sensitive to parameter selected from the group consisting of electromagnetic radiation, magnetic field, light, motion, temperature, pressure, sound, oxygen concentration, carbon dioxide concentration and moisture.

14. A metered dose inhaler according to claim 12, wherein the third sensor responds to actuation of the inhaler.

15. A metered dose inhaler for dispensing metered doses of medicament comprising:
(i) a housing having an outlet;
(ii) an aerosol container locatable within said housing, wherein the container;
(a) contains a plurality of metered doses of medicament, and
(b) has a dispensing means actuable to cause, in use, dispensing of a metered dose of the medicament from the container through the outlet;
(iii) an electronic dose counter associated with said outlet, which comprises:
a sensor for directly detecting a metered dose dispensed from said container through said outlet, said sensor comprising an emitter to emit electromagnetic radiation and a detector to detect the electromagnetic radiation emitted by the emitter, the emitter being arranged to emit the electromagnetic radiation such that it is interfered with by a metered dose of the medicament being dispensd from the container through the outlet whereby the sensor is able to detect said dispensing of the metered medicament dose, and
a visual display unit for displaying the number of metered doses of medicament used or remaining within the container in response to the sensor detecting dispensing of a metered medicament does, and
a second sensor for detecting a medicament release and wherein the first and/or second sensors are integral with the outlet.

16. A metered dose inhaler for dispensing metered doses of medicament comprising:
(i) a housing having an outlet;
(ii) an aerosol container locatable within said housing, wherein the container;
(a) contains a plurality of metered doses of medicament, and
(b) has a dispensing means actuable to cause, in use, dispensing of a metered dose of the medicament from the container through the outlet; and
(iii) an electronic dose counter associated with said outlet, which comprises:
a sensor for directly detecting a metered dose dispensed from said container through said outlet, said sensor comprising an emitter to emit electromagnetic radiation and a detector to detect the electromagnetic radiation emitted by the emitter, the emitter being arranged to emit the electromagnetic radiation such that it is interfered with by a metered dose of the medicament being dispensd from the container through the outlet whereby the sensor is able to detect said dispensing of the metered medicament dose,
a visual display unit for displaying the number of metered doses of medicament used or remaining within the container in response to the sensor detecting dispensing of a metered medicament does, and a second sensor for detecting a medicament release, wherein the first and/or second sensors are reversibly attachable to the outlet.

17. A metered dose inhaler according to claim 12, wherein the third sensor is integral with the housing.

18. A metered dose inhaler according to claim 12, wherein the third sensor is reversibly attachable to the housing.

19. A medicament dispenser comprising:
(i) a housing having an outlet;
(ii) a medicament container locatable within said housing;
(iii) an electronic dose counter associated with said outlet, wherein said dose counter includes a first sensor comprising an emitter and a detector for detecting a medicament release dispensable from said medicament container through said outlet, characterized in that the detector detects electromagnetic radiation in the infra red range, wherein the dispenser further comprises one or more optical wave guides.

20. A medicament dispenser according to claim 19, wherein the one or more optical wave guides are located on the housing.

21. A medicament dispenser according to claim 19, wherein the optical wave guide is composed of an organic polymeric or inorganic glass fibre material.

22. A medicament dispenser according to claim 19, wherein the medicament dispenser comprises a first and a second optical wave guide per sensor.

23. A medicament dispenser according to claim 22, wherein the first optical wave guide channels radiation from the emitter to the outlet.

24. A medicament dispenser according to claim 22, wherein the second optical wave guide channels radiation from the outlet to the detector.

25. A medicament dispenser comprising:
(i) a housing having an outlet;
(ii) a medicament container locatable within said housing;
(iii) an electronic dose counter associated with said outlet, wherein said dose counter includes a first sensor comprising an emitter and a detector for detecting a medicament release dispensable from said medicament container through said outlet, characterized in that the detector detects electromagnetic radiation in the infra red range, wherein the emitter and detector are located on the same side of the outlet
wherein the radiation emitted from the emitter is reflected back to the detector by a reflective surface on the opposite side of the outlet to the emitter and detector.

26. A medicament dispenser according to claim 25, wherein the reflective surface is a surface of the outlet or is an additional component attached thereto.

27. A medicament dispenser comprising:
(i) a housing having an outlet;
(ii) a medicament container locatable within said housing;
(iii) an electronic dose counter associated with said outlet wherein said dose counter includes a first sensor comprising an emitter and a detector for detecting a medicament release dispensable from said medicament container through said outlet, characterized in that the detector detects electromagnetic radiation in the infra red range, wherein the first sensor is controlled by a digital or computational semi-conductor device.

28. A medicament dispenser according to claim 27, wherein the digital or computational semi-conductor device energizes the first sensor and associated electronic components to detect and respond to a medicament release every 10 to 100 ms.

29. A medicament dispenser according to claim 27, wherein the sensor and associated electronic components are energized for 5 to 30 µs.

30. A medicament dispenser according to claim 27, wherein the digital or computational semiconductor device returns the sensor to low power mode after energizing the sensor.

31. A metered dose inhaler for dispensing metered doses of medicament comprising:
(i) a housing having an outlet;
(ii) an aerosol container locatable within said housing, wherein the container;
(a) contains a plurality of metered doses of medicament, and
(b) has a dispensing means actuable to cause, in use, dispensing of a metered dose of the medicament from the container through the outlet;
characterized by the inhaler further comprising:
(iii) an electronic dose counter associated with said outlet, which comprises:
a sensor for directly detecting a metered dose dispensed from said container through said outlet, said sensor comprising
an emitter to emit electromagnetic radiation and a detector to detect the electromagnetic radiation emitted by the emitter, the emitter being arranged to emit the electromagnetic radiation such that it is interfered with by a metered dose of the medicament being dispensd from the container through the outlet whereby the sensor is able to detect said dispensing of the metered medicament dose, and
a visual display unit for displaying the number of metered doses of medicament used or remaining within the container in response to the sensor detecting dispensing of a metered medicament does
wherein the inhaler is actuable by the application of non-mechanical energy to a coupling element and
wherein the coupling element is one or more shape memory alloy wires.

32. A housing for receipt of a medicament container, the housing comprising:
(i) an outlet for dispensing medicament therethrough; and
(ii) a first and second strand of optical wave guide associated therewith, wherein said first and second strand of optical wave guide are associable with an electronic dose counter including a first sensor for detecting medicament release through said outlet.

* * * * *